Figure 1:
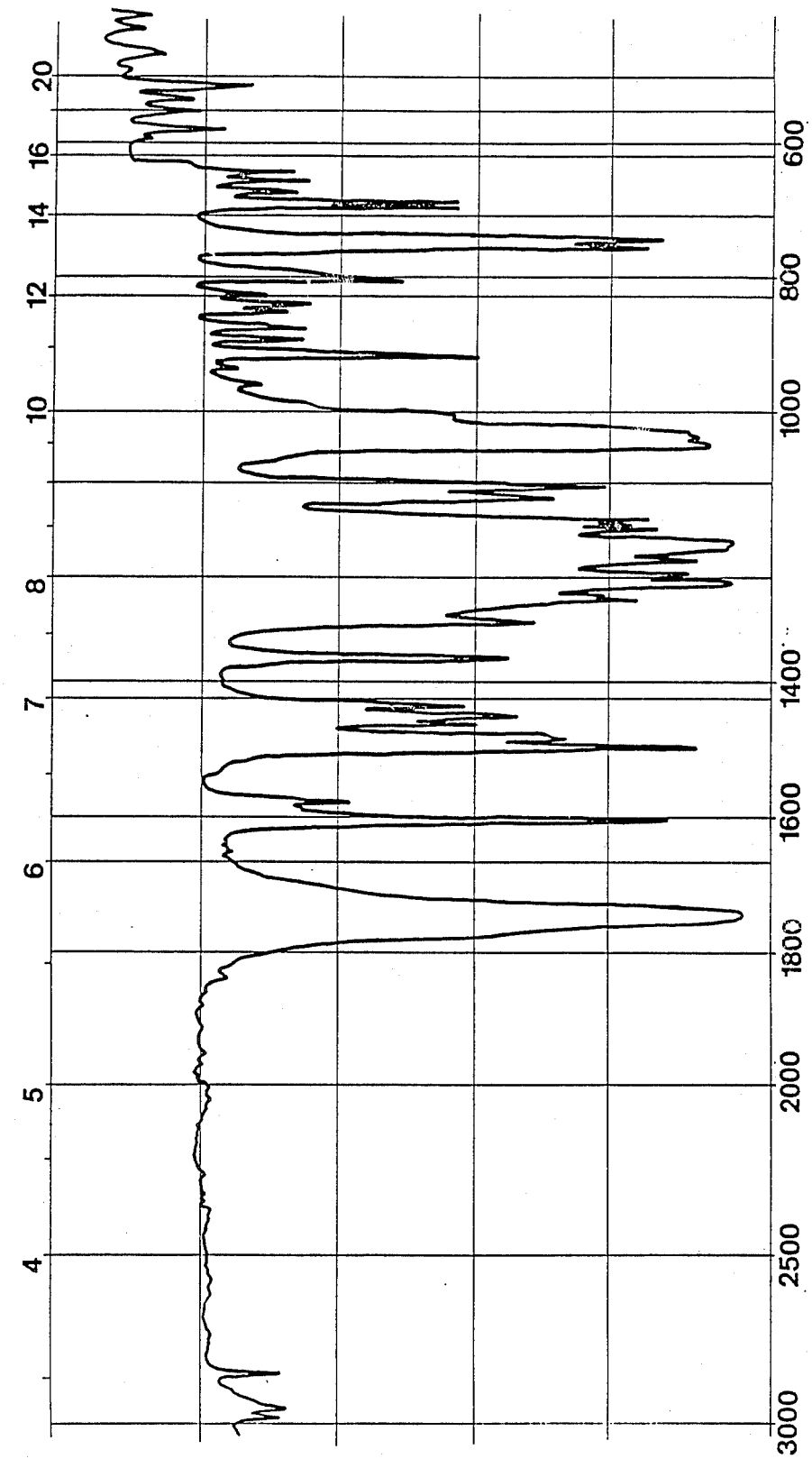

United States Patent [19]

Nicolini

[11] Patent Number: 4,743,704

[45] Date of Patent: May 10, 1988

[54] ESTERS OF SALSALATE WITH GUAIACOL, FOR TREATING PHLOGISTIC BRONCHOPNEUMOPATHIES

[75] Inventor: Marino Nicolini, Padova, Italy

[73] Assignee: FINTECO Srl, Italy

[21] Appl. No.: 63,995

[22] Filed: Jun. 19, 1987

[30] Foreign Application Priority Data

Jul. 3, 1986 [IT] Italy ............................ 21021 A/86

[51] Int. Cl.$^4$ .......................................... C07C 69/76
[52] U.S. Cl. .................................................. 560/066
[58] Field of Search ........................ 560/66; 574/133

[56] References Cited

FOREIGN PATENT DOCUMENTS 49-54340 5/1974 Japan ..................................... 16/C52

OTHER PUBLICATIONS

CA 81(21): 135728m 1974.

Primary Examiner—Paul J. Killos
Attorney, Agent, or Firm—Parkhurst & Oliff

[57] ABSTRACT

Esters of salsalate with guaiacol for treatment of phlogistic bronchopneumopathies, having the following general formula:

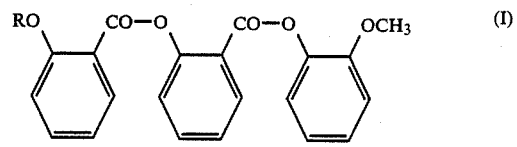

in which R is H or $CH_3CO$. Said esters combine antiphlogistic and antitussive therapeutic characteristics with high stability at gastric pH.

20 Claims, 6 Drawing Sheets

ESTERS OF SALSALATE WITH GUAIACOL, FOR TREATING PHLOGISTIC BRONCHOPNEUMOPATHIES

This invention relates to esters of salsalate with guaiacol for treating phlogistic bronchopneumopathies, their preparation process and pharmaceutical compositions which contain them as active principles.

Said esters are particularly interesting in that in addition to antiphlogistic and antitussive therapeutic characteristics, they also possess high stability towards gastric pH.

Moreover, because of the simplicity of its operating conditions and its high yields, the preparation process is convenient for implementation on an industrial scale.

Phlogistic bronchopneumopathies have complex clinical symptoms in which the local inflammatory phenomenon, characterised by bronchial hypersecretion and consequent stimulation of cough reappearance, is accompanied by systemic phlogistic symptoms such as hyperthermia and diffuse pains.

Therapy is generally effected by mutual association of antitussives, expectorants, analgesics and in particular antibiotics, with the known epidemiologic implication deriving therefrom due to the appearance of resistant strains.

These associations also involve practical difficulty in dosing the various components, in the sense of choosing the optimum dose and its constancy.

A contribution to the solution of these problems has been made by introducing the ester of acetylsalicylic acid with guaiacol into the treatment of bronchopneumopathies.

Said ester, consisting of equimolar quantities of acetylsalicylic acid and guaiacol, ensures a constant weight ratio of the two components, the first of which is of antiphlogistic activity and the second of which is of antitussive activity.

However, from the practical treatment aspect this ester has drawbacks deriving from its poor stability at the oral and gastric level, because of which on the one hand it gives rise to unpleasant odour and taste and on the other hand at the gastric level it exerts the known ulcerogenic action of acetylsalicylic acid.

These drawbacks are obviated by the use in the treatment of phlogistic bronchopneumopathies of the esters of salsalate with guaiacol according to the present invention, which besides having a therapeutic activity equal to that of the ester of acetylsalicylic acid with guaiacol have the great advantage of being particularly stable and of not dissociating either at the oral or at the gastric level, but only at the intestinal level where they are rapidly absorbed.

Thus the organoleptic characteristics are considerably improved, and in particular the ulcerogenic action which occurs in the use of the ester of acetylsalicylic acid with guaiacol is obviated.

The esters of salsalate with guaiacol according to the present invention have the following general formula:

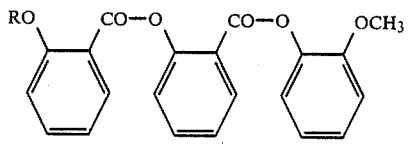

in which R is H or CH₃CO.

The process for preparing compounds of general formula (I) comprises the following stages:

(a) treating 2-hydroxy-benzoylchloride with guaiacol salicylate, to obtain guaiacol salsalate (II) in accordance with the reaction:

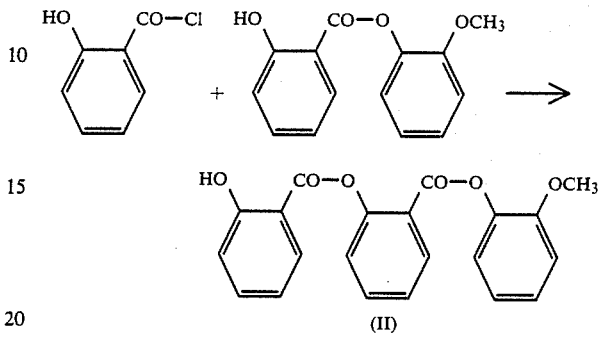

(b) treating the guaiacol salsalate (II) with acetic anhydride to obtain guaiacol acetylsalsalate (III) in accordance with the reaction:

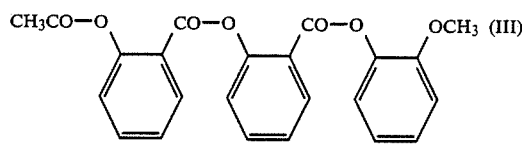

In stage (a) the 2-hydroxybenzoylchloride is dissolved in an organic solvent, preferably 1,2-dichloroethane, the solution is cooled to a temperature of between −2° and +2° C., and N,N-dimethylaniline and guaiacol salsalate are added under energetic agitation.

A 20-50% molar excess of 2-hydroxybenzoylchloride with respect to the guaiacol salsalate is used.

The mixture obtained is reacted for 5-10 hours at a temperature of between 35° and 45° C. under agitation.

The guaiacol salsalate produced is separated from the mixture by known methods, for example by adding water to the reaction mixture, separating the organic phase from the aqueous phase, concentrating the organic phase and crystallising the product from isopropanol.

The yield is very high, generally about 80%. In stage (b) the guaiacol salsalate and acetic anhydride are mixed together in a molar ratio of between 20 and 40, and pyridine is added to the mixture as catalyst.

The mixture is reacted at 55°-65° C. for 2-3 hours and is then poured into cold water and kept under agitation for 2 hours.

The guaiacol acetylsalsalate produced is separated from the mixtures by known methods, for example by pouring the reaction mixture into water, filtering off the product and crystallising it from isobutyl-methylketone.

The yield is very high, generally about 90%.

As an alternative to stage (a), the guaiacol salsalate (II) can be prepared by reacting salicylic acid with guaiacol salsalate in a molar ratio preferably of 1:1, in the presence of phosphorus oxychloride in a reaction medium consisting of dimethylformamide.

The reaction is conducted at 60°–70° C. under agitation for 1–2 hours.

As an alternative to preparing guaiacol acetylsalsalate (II) as described in stage (b), this product can be obtained by reacting O-acetoxybenzoylchloride with guaiacol salsalate in accordance with the following equation:

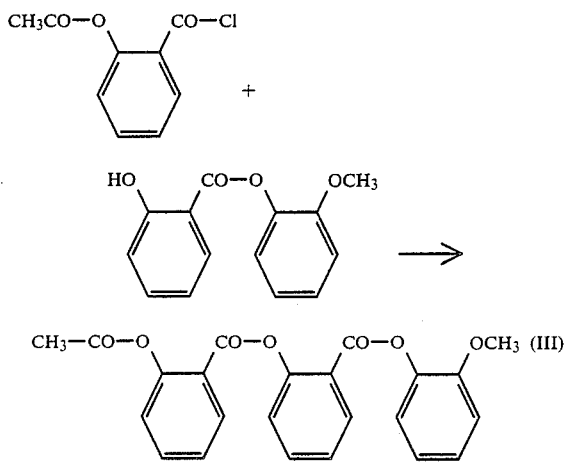

Each of the two reagents is dissolved in methylene chloride, triethylamine is added to the guaiacol salsalate, and the two solutions are mixed together under slow agitation at a temperature of 0°–5° C. The reaction is conducted at this temperature for 3–6 hours.

The molar reagent ratio is preferably 1:1. The yield is very high, generally about 95%.

It is very convenient to prepare the salsalate (II) industrially by a deacetylation reaction from the acetylsalsalate (II) obtained by the described alternative method. This reaction can be carried out by treating (III) at 85°–95° C. in a mixture of acetone and an aqueous concentrated HCl solution in a volumetric ratio of 1:1 for 3–5 hours, then cooling to ambient temperature and treating with water. Both the product (II) and its acetyl derivative (III) find application in the treatment of phlogistic bronchopneumopathies. Both are stable at stomach pH.

The following examples of the preparation of guaiacol salsalate and guaiacol acetylsalsalate are given for the purpose of nonlimitative illustration of the invention.

EXAMPLE 1

(a) Preparation of guaiacol salsalate 121 g of N,N-dimethylaniline and 244 g of guaiacol salicylate (1.0 mole) are added under energetic agitation to a solution, cooled to 0° C., of 200 g of 2-hydroxybenzoylchloride (1.3 moles) in 1 liter of 1,2-dichloroethane.

The mixture is heated to 40° C. and kept under agitation for 6 hours. 0.5 liters of water are rapidly added, the phases are allowed to stratify and the organic phase is separated and washed with water, then concentrated to dryness under reduced pressure. The oily residue is crystallised from isopropanol to obtain an overall yield of 80%.

The product has a melting point of 86° C. It is characterised by infrared, ultraviolet and NMR spectrography, and the spectra obtained are shown respectively in FIGS. 1, 2 and 3.

Figure 2:
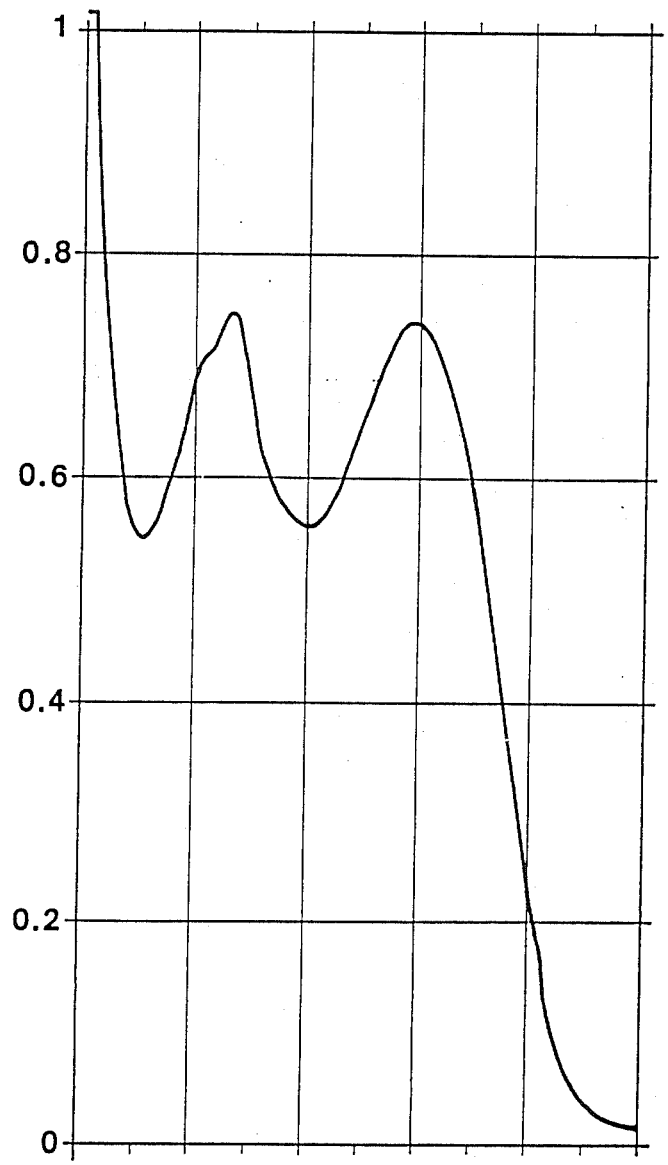
Figure 3:
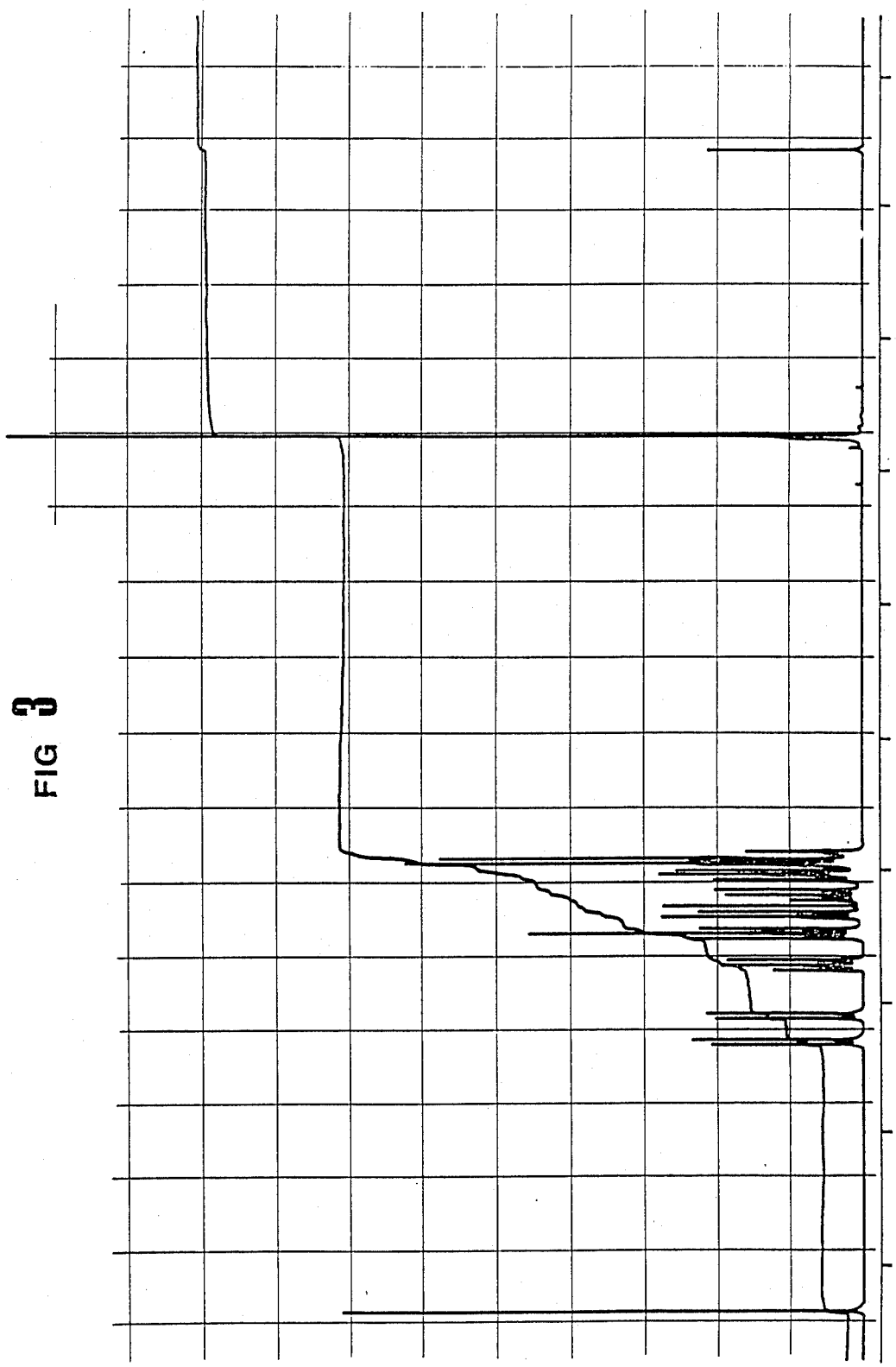

Specifically:

in FIG. 1, the lower abscissa represents the wave number expressed in cm$^{-1}$, the upper abscissa represents the wavelength expressed in microns, and the ordinate represents transmittance (%).

in FIG. 2, the abscissa represents the wavelength λ expressed in nanometers, and the ordinate represents absorbance.

in FIG. 3, the abscissa represents the chemical shift in δ.

(b) Preparation of guaiacol acetylsalsalate

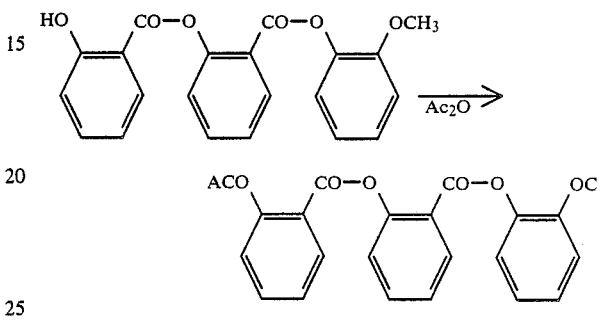

364 g of guaiacol salsalate (1.0 mole) are added to 200 ml of acetic anhydride (2.1 moles) and 20 ml of pyridine as catalyst. The mixture is heated to 60° C. for 3 hours monitoring the progress of the reaction chromatographically.

The mixture is then poured into 2 liters of cold water and kept under agitation for 2 hours. After filtration, the product is washed abundantly with water, then crystallised from isobutyl-methyl-ketone to obtain an overall yield of 90%.

The product has a melting point of 131°–132° C.

Figure 4:
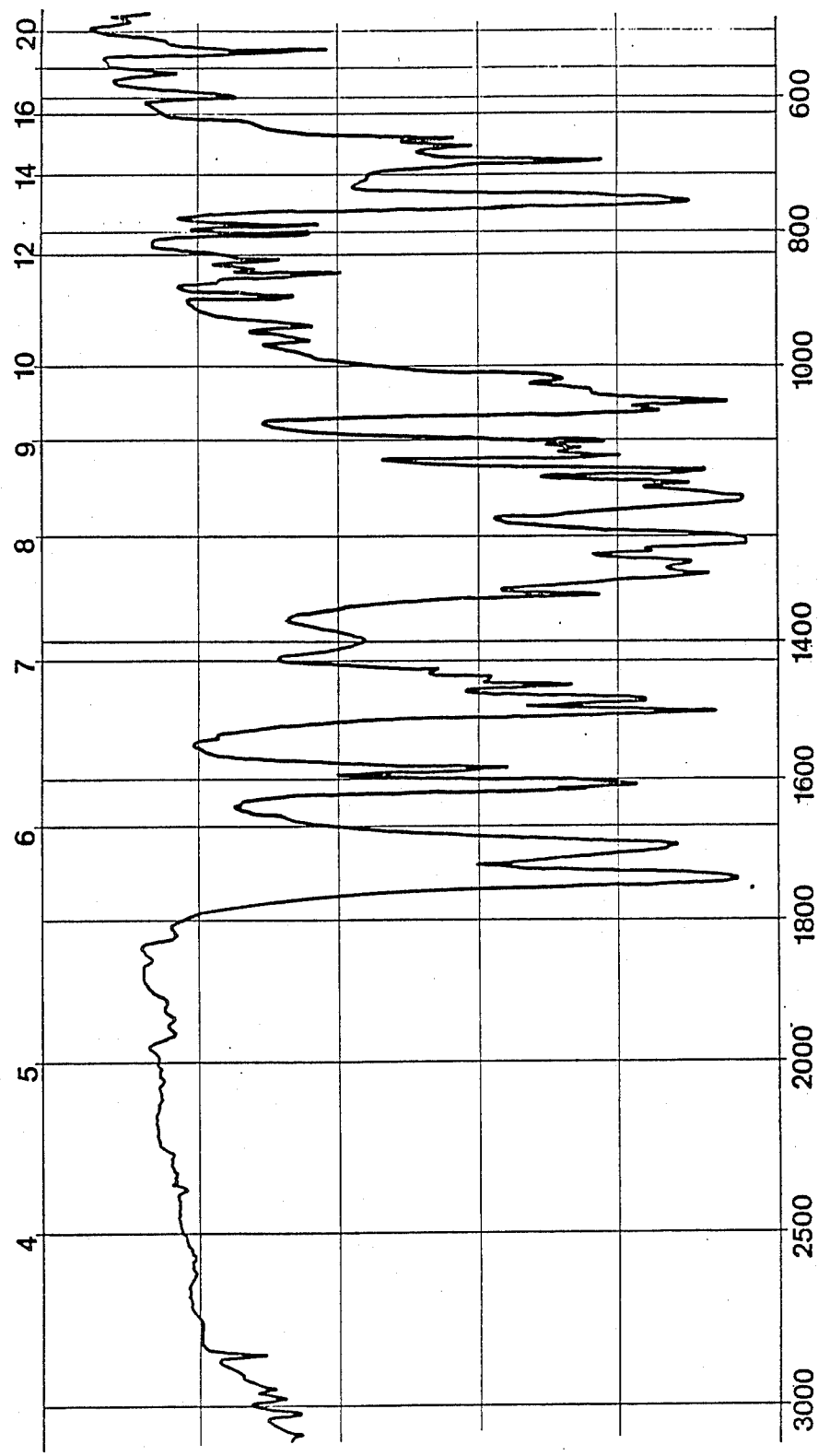
Figure 5:
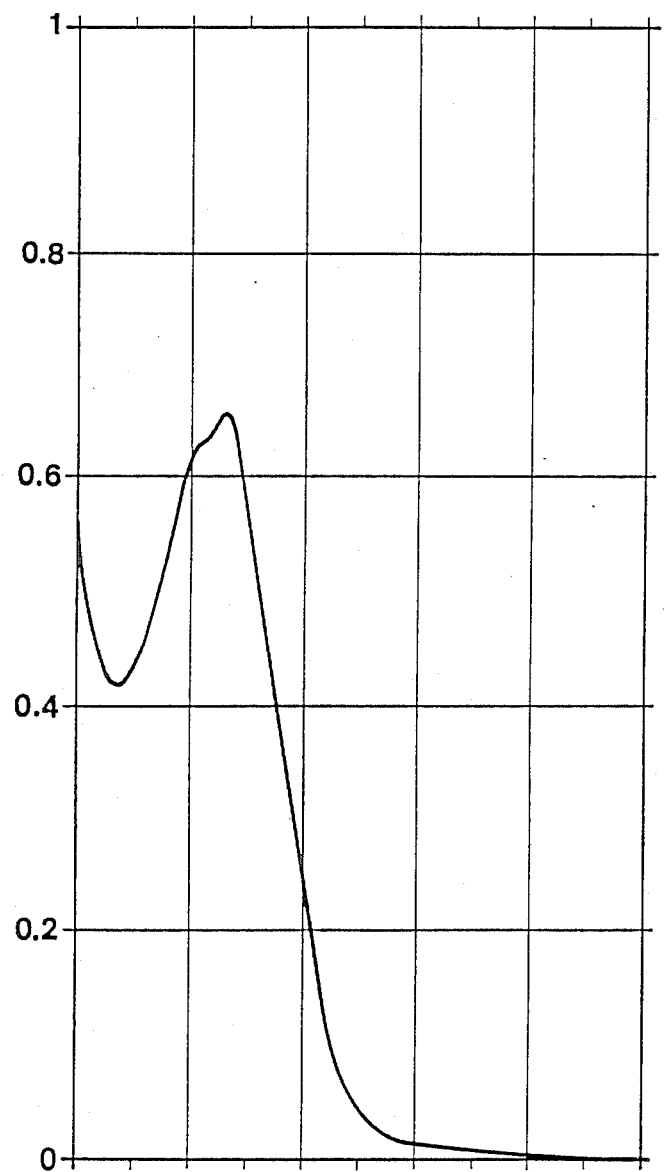
Figure 6:
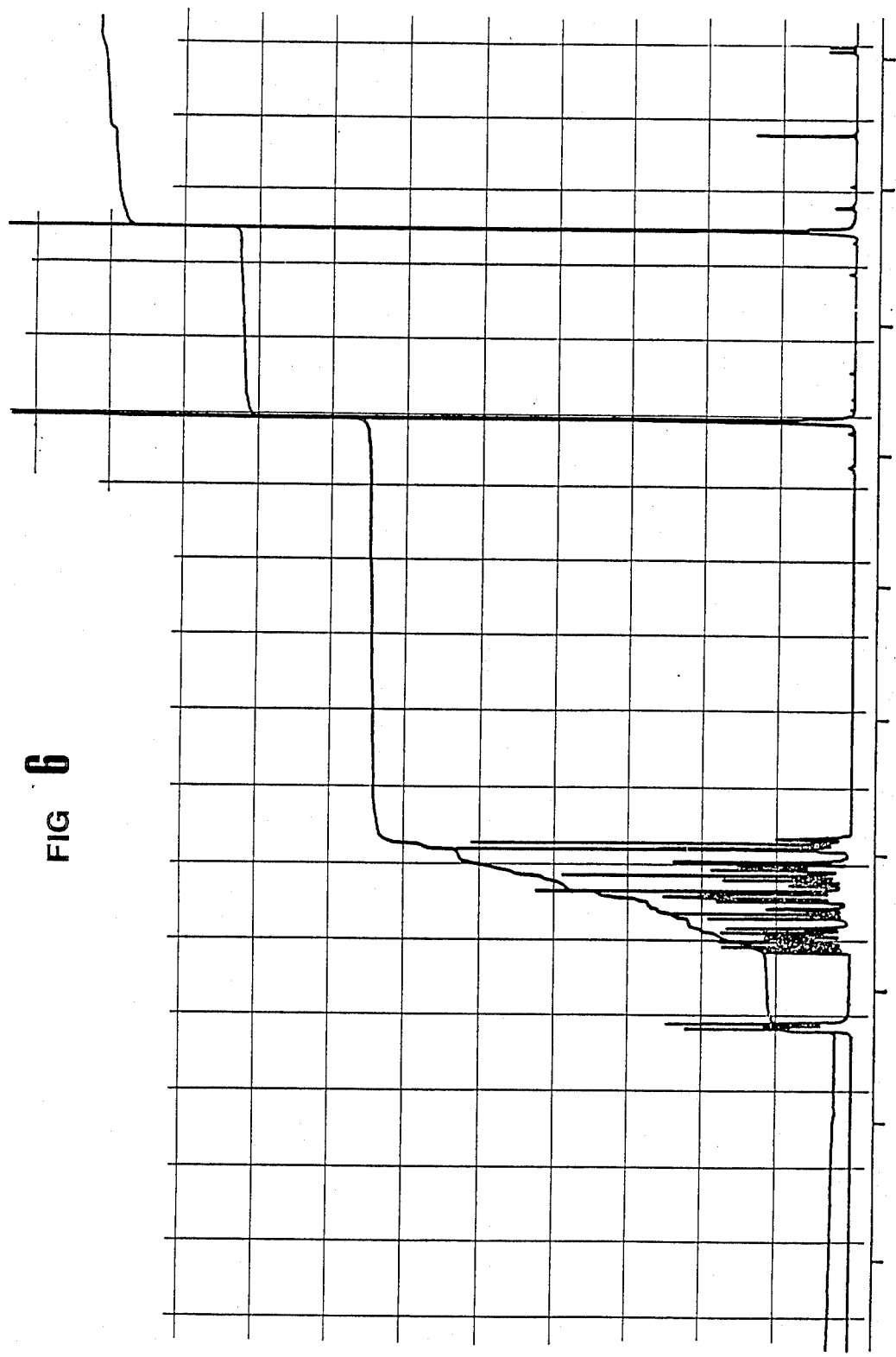

It is characterised by infrared, ultraviolet and NMR spectrography, and the spectra obtained are shown in FIGS. 4, 5 and 6 respectively.

Specifically:

in FIG. 4, the lower abscissa represents the wave number expressed in cm$^{-1}$, the upper abscissa represents the wavelength expressed in microns, and the ordinate represents transmittance (%).

in FIG. 5, the abscissa represents the wavelength λ expressed in nanometers, and the ordinate represents absorbance.

in FIG. 6, the abscissa represents the chemical shift in δ.

EXAMPLE 2

Preparation of guaiacol salsalate 244 g of guaiacol salicylate (1.0 mole) and 138 g of salicylic acid (1.0 mole) are suspended in 1 liter of dimethylformamide. 80 g of phosphorus oxychloride are added over a period of about one hour to the solution, which is kept heated under agitation to 60°–70° C., and the mixture is maintained at this temperature until hydrochloric acid ceases to be evolved. The homogeneous dense mass, of straw colour, is poured under energetic agitation into 5 liters of a water-ice mixture and the suspension is neutralised slowly with dilute sodium hydroxide. The crystalline white solid which precipitates is filtered off, washed abundantly with water and then crystallised from isopropanol to obtain an overall yield of 60%. The product has a melting point of 85°–86° C.

EXAMPLE 3

Preparation of guaiacol acetylsalsalate 224 g of guaiacol salsalate (1.0 mole) and 102 g of triethylamine are dissolved in 1 liter of methylene chloride. A solution of 197 g of freshly distilled O-acetoxybenzoylchloride (1.0 mole) in 0.5 liters of methylene chloride are added to the solution, which is under agitation at a temperature of 0°-2° C., the addition being made slowly such that the mixture temperature does not exceed 5° C. After about 4 hours at this temperature, 0.5 liters of water are added, agitation is applied energetically, and the phases are allowed to stratify. The lower organic phase is separated and concentrated under reduced pressure, the residue being taken up in 0.6 liters of ethanol. The white crystalline solid which separates is filtered off, washed with cold ethanol, and then crystallised from isobuty-methyl-ketone to obtain 385 g of product with a yield of 95%. The product has a melting point of 131°-132° C.

Analysis for $C_{23}H_{18}O_7$: C 68.98%; H 4.46%
Found: C 67.96%; H 4.45%

EXAMPLE 4

Preparation of guaiacol salsalate by deacetylation of guaiacol acetylsalsalate 41 g of guaiacol acetylsalsalate are dissolved in 300 ml of a 1:1 volume mixture of acetone and a 35 weight% HCl solution, the mixture being heated to 90° C. for 4 hours under agitation.

It is cooled, 300 ml of water are added and the deacetylated product filtered off, and then crystallised from 100 ml of isopropanol.

Pure guaiacol salsalate is obtained in this manner with a yield of 80%.

We claim:

1. Esters of salsalate with guaiacol for treatment of phlogistic bronchopneumopathies, having the following general formula:

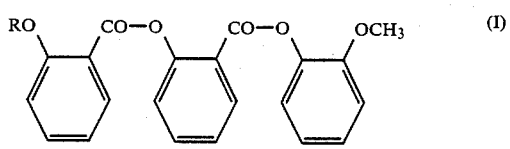

in which R is H or $CH_3CO$.

2. A process for preparing esters of salsalate with guaiacol for treatment of phlogistic bronchopneumopathies, having the following general formula:

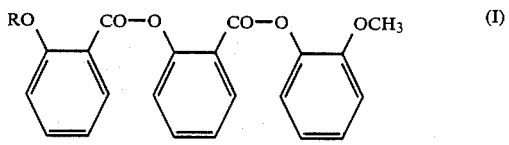

in which R is H or $CH_3CO$, characterised in that in a first stage 2-hydroxy-benzoylchloride is treated with guaiacol salicylate to obtain guaiacol salsalate (II) in accordance with the reaction:

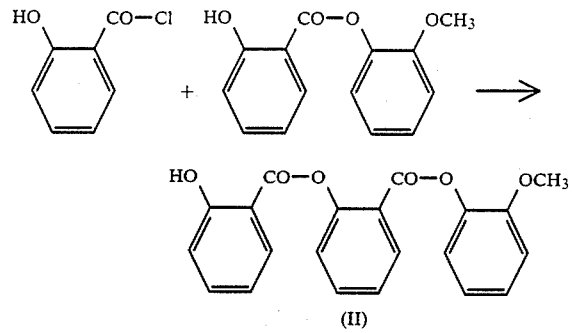

and in a second stage the guaiacol salsalate (II) is treated with acetic anhydride to obtain guaiacol acetylsalsalate (III) in accordance with the reaction:

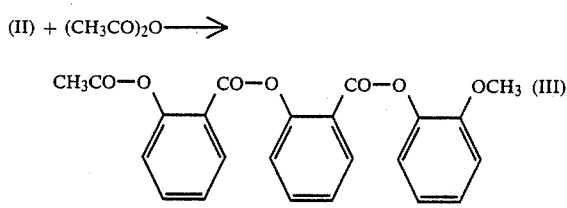

3. A process as claimed in claim 2, characterised in that said first stage reaction is conducted in a medium consisting of an organic solvent in the presence of N,N-dimethylaniline.

4. A process as claimed in claim 2, characterised in that said first stage reaction is conducted in a medium consisting of 1,2-dichloroethane.

5. A process as claimed in claim 2, characterised in that said first stage reaction is conducted with a 20-50% molar excess of 2-hydroxy-benzoylchloride with respect to the guaiacol salicylate.

6. A process as claimed in claim 2, characterised in that said first stage reaction is conducted at a temperature of between 35° and 45° C. under agitation for 5-10 hours.

7. A process as claimed in claim 2, characterised in that said said second stage reaction is conducted in the presence of pyridine as catalyst.

8. A process as claimed in claim 2, characterised in that said second stage reaction is conducted with a molar ratio of guaiacol salsalate to acetic anhydride of between 2.0 and 4.0.

9. A process as claimed in claim 2, characterised in that said second stage reaction is conducted at a temperature of between 55° and 65° C. for 2-3 hours.

10. A process for preparing guaiacol salsalate (II) by reacting salicylic acid with guaiacol salicylate in the presence of phosphorus oxychloride in a reaction medium consisting of dimethylformamide.

11. A process as claimed in claim 10, characterised in that said reaction is conducted with a molar ratio of salicylic acid to guaiacol salicylate equal to 1:1.

12. A process as claimed in claim 10, characterised in that said reaction is conducted at a temperature of between 60° and 70° C. for 1-2 hours.

13. A process for preparing guaiacol acetylsalsalate (III) by reacting O-acetoxybenzoylchloride with guaiacol salicylate in the presence of triethylamine in a reaction medium consisting of methylene chloride.

14. A process as claimed in claim 13, characterised in that said reaction is conducted with a molar reagent ratio of 1:1.

15. A process for preparing guaiacol salsalate by deacetylation of guaiacol acetylsalsalate by treating this latter with a mixture of acetone and concentrated HCl, followed by treatment with water.

16. A process as claimed in claim 15, characterised in that said mixture of acetone and HCl is formed from acetone and an aqueous 35 weight% HCl solution in a volume ratio of 1:1.

17. A process as claimed in claim 15, characterised in that said treatment with the mixture of acetone and concentrated HCl is conducted at 85°–95° C.

18. A process as claimed in claim 15, characterised in that said treatment with water is conducted at ambient temperature.

19. A process as claimed in claim 13, characterised in that said reaction is conducted at a temperature of between 0° and 5° C. for 3–6 hours.

20. Pharmaceutical compositions for phlogistic bronchopneumopathy treatment containing as active principles esters of salsalate with guaiacol having the following general formula:

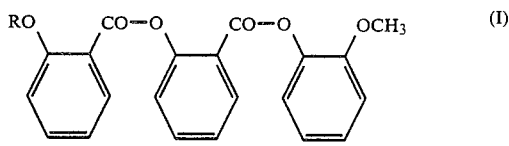

in which R is H or $CH_3CO$.

UNITED STATES PATENT AND TRADEMARK OFFICE
CERTIFICATE OF CORRECTION

PATENT NO. : 4,743,704

DATED : May 10, 1988

INVENTOR(S) : Marino Nicolini and Angelo Signor

It is certified that error appears in the above-identified patent and that said Letters Patent is hereby corrected as shown below:

On the cover page, after "[75] Inventor: Marino Nicolini," insert --and Angelo Signor, both of--.

Signed and Sealed this

Twentieth Day of December, 1988

Attest:

DONALD J. QUIGG

*Attesting Officer*  *Commissioner of Patents and Trademarks*